United States Patent [19]

Reed

[11] Patent Number: 4,617,278

[45] Date of Patent: Oct. 14, 1986

[54] PETROLEUM ALCOHOL TEST KIT AND METHOD OF TESTING PETROLEUM FOR ALCOHOL CONTENT

[75] Inventor: Dennis A. Reed, Fort Wayne, Ind.

[73] Assignee: Bert Keenan, Fort Wayne, Ind.

[21] Appl. No.: 782,997

[22] Filed: Oct. 1, 1985

[51] Int. Cl.$^4$ ........................................... G01N 33/22
[52] U.S. Cl. ....................................... 436/60; 422/61;
   436/128; 436/132; 436/181
[58] Field of Search ........................ 422/58, 61, 102;
   436/60, 128, 130-132, 169, 181

[56] References Cited

U.S. PATENT DOCUMENTS

| | | | |
|---|---|---|---|
| 1,674,416 | 6/1928 | Taylor | 422/61 X |
| 1,689,901 | 10/1928 | Williams . | |
| 2,265,196 | 12/1941 | Riley | 436/128 X |
| 2,844,025 | 7/1958 | Joyce et al. | 436/60 X |
| 3,208,827 | 9/1965 | Borkenstein | 436/132 |
| 3,272,319 | 9/1966 | Brewer | 206/12 |
| 3,528,775 | 9/1970 | O'Hara et al. | 422/61 X |
| 3,711,251 | 1/1973 | Goodson et al. | 436/128 X |
| 3,888,628 | 6/1975 | Graham | 436/132 |
| 3,899,298 | 8/1975 | Szczesniak | 424/1 X |
| 4,011,350 | 3/1977 | Markovits et al. | 427/2 |
| 4,097,240 | 6/1978 | Hirsch | 436/128 X |
| 4,105,409 | 8/1978 | Monnier et al. | 436/132 |
| 4,174,202 | 11/1979 | Simpson | 422/61 X |
| 4,184,850 | 1/1980 | Habenstein | 436/128 |
| 4,239,746 | 12/1980 | Bartos et al. | 424/12 |
| 4,303,610 | 12/1981 | Sardisco et al. | 422/61 |

FOREIGN PATENT DOCUMENTS

| | | | |
|---|---|---|---|
| 2608062 | 8/1977 | Fed. Rep. of Germany | 436/131 |
| 3205976 | 9/1983 | Fed. Rep. of Germany | 436/60 |
| 48553 | 5/1981 | Japan | 436/132 |

OTHER PUBLICATIONS

J.A.M.A., vol. 170, No. 1, May 2, 1959, pp. 47-71, "Chemical Testing Procedures for the Determination of Ethyl Alcohol", Friedemann et al.

*Primary Examiner*—Robert Spitzer
*Attorney, Agent, or Firm*—Jeffers, Irish & Hoffman

[57] ABSTRACT

A petroleum alcohol test kit and a method of testing petroleum for alcohol content both as to volume and type. The volume of alcohol present is determined by mixing a petroleum sample with a first colorimetric solution whereby the volume of alcohol can be visually determined. The type of alcohol present is determined by mixing the components of a second colorimetric solution for impregnation of a visual indicator. A petroleum sample is mixed with an acidified potassium permanganate solution and the resultant vapors contact the visual indicator whereby the color the indicator turns is indicative of the type of alcohol present. The kit has the necessary containers, support and solutions to carry out the testing.

18 Claims, 7 Drawing Figures

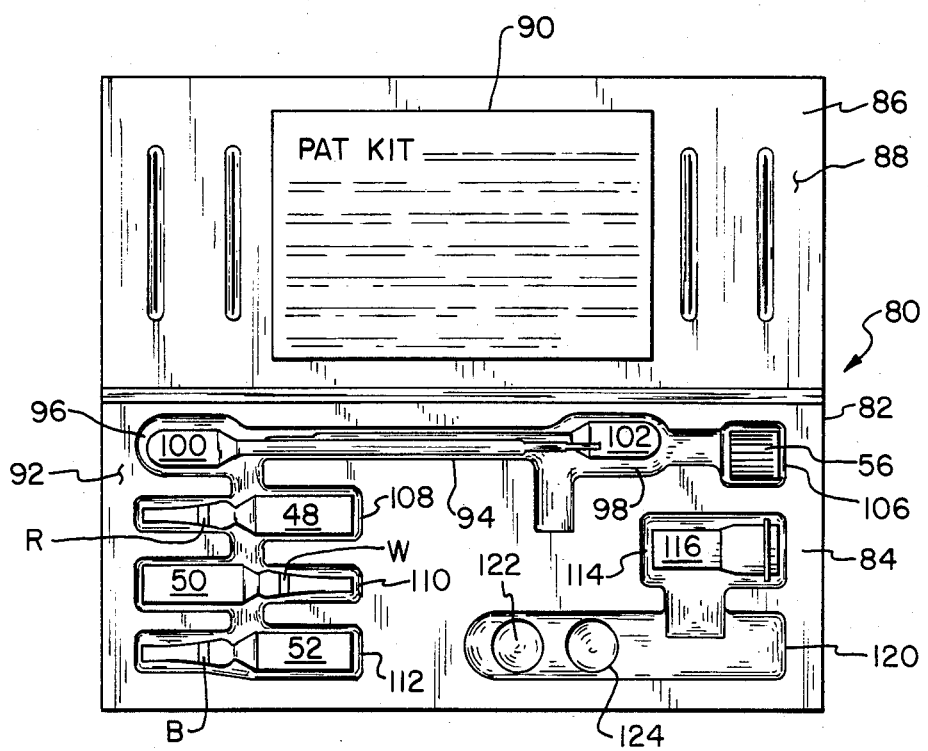
FIG. 4
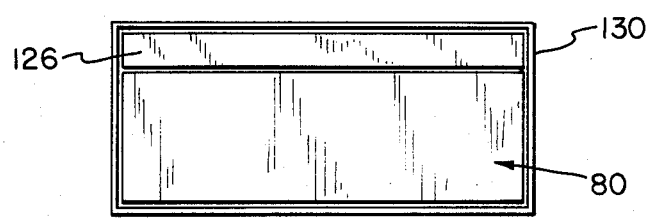
FIG. 7
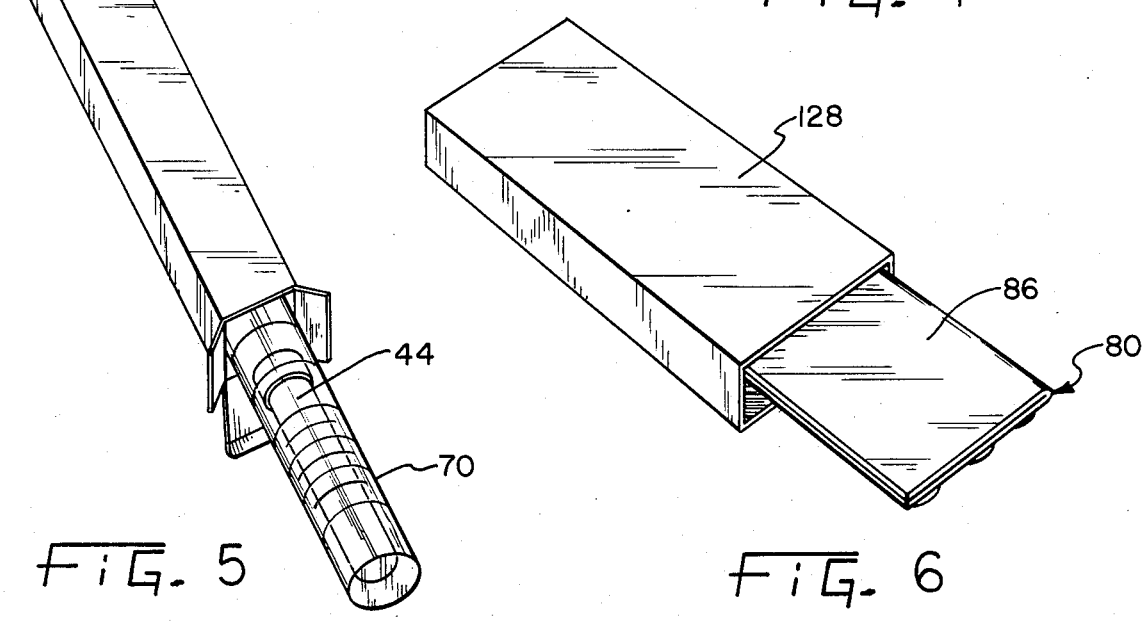
FIG. 5
FIG. 6

4,617,278

PETROLEUM ALCOHOL TEST KIT AND METHOD OF TESTING PETROLEUM FOR ALCOHOL CONTENT

BACKGROUND OF THE INVENTION

The invention relates to a petroleum test kit and method for testing petroleum, and more specifically, to an on site petroleum alcohol test kit and method for testing petroleum wherein the amount of alcohol and the kind of alcohol can be determined.

In an effort to achieve energy independence and to avoid the fuel shortages of the early 1970's, the Federal government instituted tax credits and other incentives for the use of ethanol as a gasoline extender. However, these well-intentioned incentives also led to substantial abuses in the amounts of alcohol and non-alcohol substances added to gasolines which, in turn, has led to problems in fuel quality control and damage to vehicle power plants by improperly blended fuels. The problem has become so widespread that car and truck manufacturers have restricted warranties on new vehicles using improper alcohol blends. For example, blends that use methanol without an EPA variance are illegal. The Environmental Protection Agency has recently sought out and fined violators. Excess alcohol content and improper alcohol blends have caused increased emissions of nitrogen oxide and hydrocarbons, which react with sunlight to produce smog.

Heretofore, it has been difficult to quickly and easily test petroleum on site for alcohol content (both as to amount and type) in a reliable fashion. Consequently, persons were never sure of the alcohol content and type of alcohol contained in the petroleum product. Because of this, purchasers of bulk petroleum products such as gasoline dealers may very well have innocently purchased a load of petroleum that does not comply with the alcohol content requirements of the EPA by containing more alcohol than permitted and/or an impermissible volume of methanol. As can be appreciated, the inability to quickly perform a reliable on-site test of the petroleum product for alcohol content is a meaningful problem to purchasers of bulk petroleum products.

SUMMARY OF THE INVENTION

Applicant's invention provides a test kit and method for testing petroleum products for alcohol content that is quick and easy and produces reliable results and can also be performed on the site so as to overcome the problems set out above.

Broadly speaking, the invention is directed to a kit for performing an alcohol content test on a petroleum product, such as gasohol, and the method of conducting such a test. The test is essentially a two step test. The first step of the test determines the amount of alcohol (both ethyl alcohol and methyl alcohol) in the sample. The second step of the test determines the type of alcohol (either ethyl alcohol or methyl alcohol) present in the sample. Further, the kit is constructed so that it is easy to use on site without the need for any further materials. Premeasured volumes of the reactants are contained in vessels.

In one form thereof, the invention is a test kit for on site testing of petroleum for alcohol content comprising a calibrated reaction cylinder, a first tube of ethylene glycol and methyl violet color indicator, a second tube having an opening sealably closable by a lid means, and a first lid means for removably sealing the opening, a first vial of 20% solution of morpholine in distilled water, and a second vial of 5% solution of sodium nitroprusside in distilled water. The kit further includes a mixing cup for mixing the contents of the first and second vials to make an indicating fluid, a second lid means for removably sealing the opening in the second tube, the second lid means includes a fluid-absorbent paper or fabric adapted to be impregnated with the indicating fluid, and a third vial of potassium permanganate and sulfuric acid in distilled water. A carrier is adapted to receive and carry the first tube, the second tube with the first lid means attached, the first, second and third vials, the mixing cup, the second lid means, and the calibrated reaction cylinder.

In another form thereof, the invention is a test kit for on site testing of gasohol for the presence of ethyl alcohol comprising, a reaction tube having an opening sealably closable by a lid means, and a first lid means for removably sealing the opening, a first vial of 20% solution of morpholine in distilled water, and a second vial of 5% solution of sodium nitroprusside in distilled water. The kit further includes a mixing cup for mixing the contents of the first and second vials to make an indicating fluid, a second lid means for removably sealing the opening in the reaction tube, the second lid means including a fluid-absorbent paper or fabric adapted to be impregnated with the indicating fluid, and a third vial of potassium permanganate and sulfuric acid in distilled water. A carrier is adapted to receive and carry the reaction tube with the first lid means attached, the first, second and third vials, the mixing cup and the second lid means.

In another form thereof, the invention is directed to a method for on site testing of petroleum for alcohol content comprising the steps of mixing a first sample of the petroleum with a first colorimetric reagent solution of ethylene glycol and methyl violet dye in a graduated cylinder, positioning said graduated cylinder in a generally vertical position, observing the mixed contents of said cylinder for the presence of a colored portion wherein the colored portion is indicative of the presence of ethyl alcohol or methyl alcohol alone or together in the petroleum, measuring the height of said colored portion to determine the amount of alcohol in the petroleum sample, mixing a 20% solution of morpholine in distilled water with a 5% solution of sodium nitroprusside in distilled water to form a second reagent colorimetrically and selectively responsive to the presence of acetaldehyde and non-responsive to the presence of formaldehyde, impregnating a fabric with the second colorimetric reagent, mixing a solution of potassium permanganate and sulfuric acid in distilled water with a second sample of petroleum, contacting the fabric with vapors emitted by the mixture of the potassium permanganate-sulfuric acid solution and second sample of petroleum, and observing the color of the colorimetric reagent, a color change occurring in response to the presence of acetaldehyde (which is the reaction product of ethyl alcohol and acidified potassium permanganate) and an absence of color change occurs in response to the presence of formaldehyde (which is the reaction product of methyl alcohol and acidified permanganate) in the second sample of petroleum.

In another form thereof, the invention is a method for on site testing of gasohol for the presence of ethyl alcohol comprising the steps of mixing a 20% solution of morpholine in distilled water with a 5% solution of sodium nitroprusside in distilled water to form a reagent colorimetrically and selectively responsive to the presence of acetaldehyde and non-responsive to the presence of formaldehyde, impregnating a fabric with said colorimetric reagent, mixing a solution of potassium permanganate and sulfuric acid in distilled water with a gasohol sample, contacting said fabric with vapors emitted by the mixture of said potassium permanganate-sulfuric acid solution and gasohol, wherein ethyl alcohol and the acidified potassium permanganate react to form acetaldehyde and methyl alcohol and the acidified potassium permanganate react to form formaldehyde, and observing the color of the colorimetric reagent wherein a color change is in response to the presence of ethyl alcohol and an absence of color change is in response to the presence of methyl alcohol.

In another form thereof, the invention is a test kit for on site testing of petroleum for alcohol content comprising a calibrated reaction cylinder removably contained within an elongate box, a first tube of ethylene glycol and methyl violet color indicator, a second tube having an opening sealably closable by a lid means, and a first lid means for removably sealing said opening. The first tube is contained within said calibrated reaction cylinder. The kit further includes a first vial of 20% solution of morpholine in distilled water, and a second vial of 5% solution of sodium nitroprusside in distilled water.

The kit also includes a mixing cup for mixing the contents of the first and second vials to make an indicating fluid and a second lid means for removably sealing the opening in the second tube. The second lid means includes a fluid-absorbent paper or fabric adapted to be impregnated with the indicating fluid. A third vial of potassium permanganate and sulfuric acid in distilled water is included in the kit. A carrier is adapted to receive and carry the second tube with the first lid means attached, the first, second and third vials, the mixing cup and the second lid means. The carrier is slideable into a sleeve to form a sleeve-carrier assembly. The elongate box and sleeve-carrier assembly are positioned withing a container.

The above-mentioned and other features and objects of this invention and the manner of attaining them will become more apparent and the invention itself will be best understood by reference to the following description of an embodiment of the invention taken in conjunction with the accompanying drawings.

BRIEF DESCRIPTION OF THE DRAWINGS

FIG. 4 is a top view of another specific embodiment of the petroleum alcohol test kit;

FIG. 5 is a perspective view of the graduated cylinder protruding from its box;

FIG. 6 is a perspective view of the specific embodiment of FIG. 4 protruding from its sleeve; and FIG. 7 is a top view of the graduated cylinder in its box and the kit in its sleeve positioned within the bottom half of a box.

DETAILED DESCRIPTION OF SPECIFIC EMBODIMENT

Figure 1:
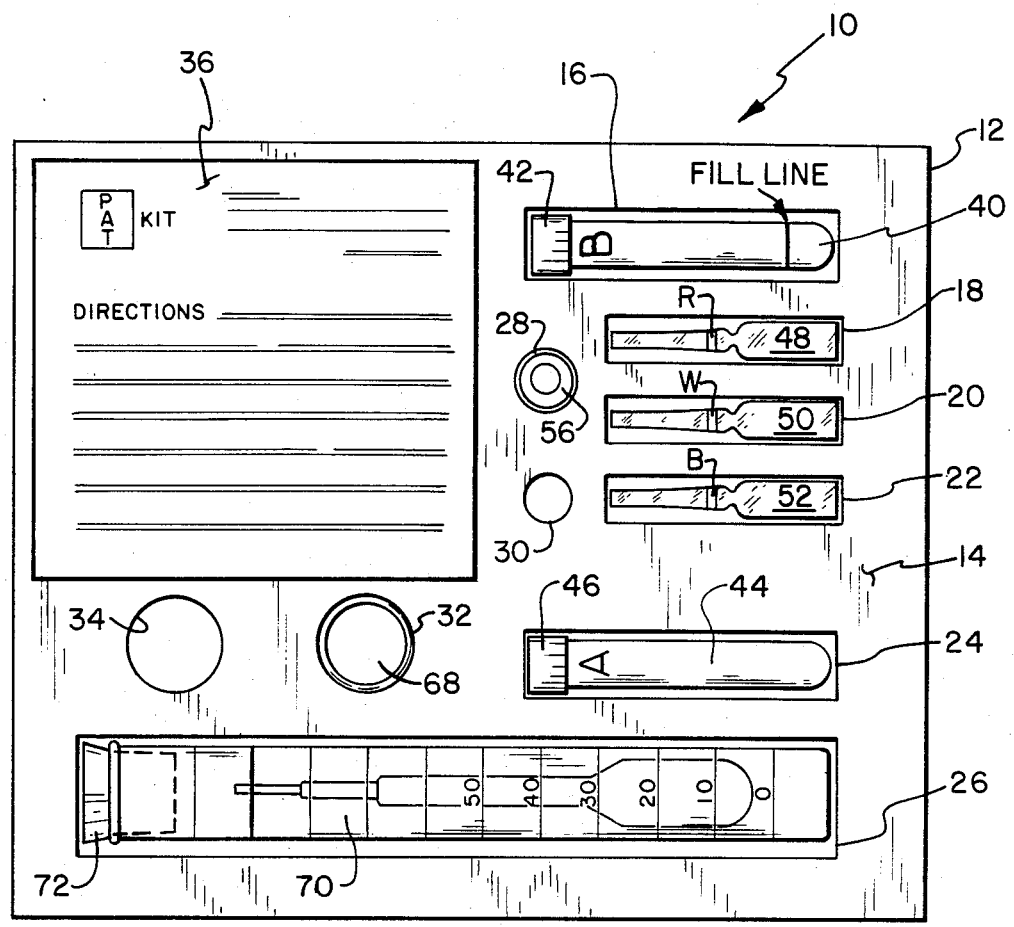
FIG. 1 is a top view of a specific embodiment of the petroleum alcohol test kit.
Figure 2:
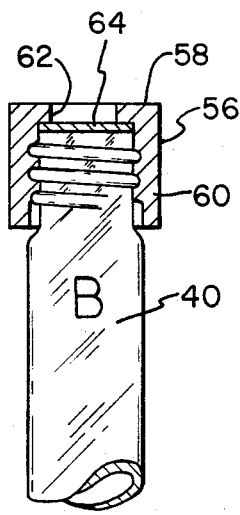
FIG. 2 is a view of the upper portion of a test tube having an indicator cap affixed thereto wherein the indicator cap is illustrated in cross-section.
Figure 3:
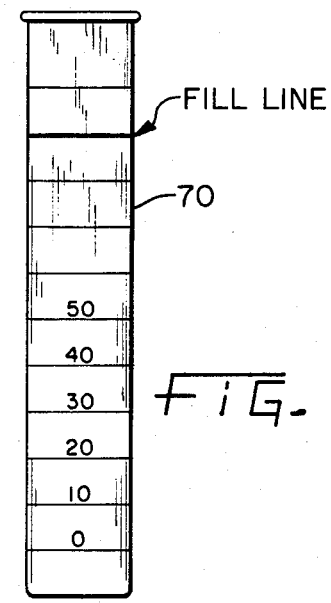
FIG. 3 is a side view of the graduated cylinder.

Referring to the drawings, there is illustrated a specific embodiment of a petroleum alcohol test kit generally designated as 10. Petroleum alcohol test kit 10 includes a base 12 made from styrofoam or a like material that is sturdy yet lightweight. There are a number of recesses contained in the top surface 14 of base 12. More specifically, elongate recesses 16, 18, 20, 22, 24 and 26 are contained in surface 14 as well as circular recesses 28, 30, 32 and 34 are contained within surface 14 of base 10. Directions for use 36 of the petroleum alcohol test kit 10 are affixed to the base 12 in the upper lefthand quadrant of the surface 14 as viewed in FIG. 1.

Petroleum alcohol test kit 10 further includes an elongate tubular container 40, having a visual indicator "B", which rests in elongate recess 16. A cap 42 is threadedly received by container 40 to selectively close the open end thereof. Another elongate tubular container 44, having a visual indicator "A", rests within elongate recess 24 and includes a cap 46 which is threadably received thereby to selectively close the open end thereof. Tubular container 44 contains 10 ml of a solution comprised of 98% by volume of ethylene glycol ($HOCH_2CH_2OH$) and 2% by volume of methyl violet dye. As will be discussed hereinafter, this solution when mixed with a petroleum sample will determine the volume of alcohol present in the sample. The ethylene glycol-methyl violet dye solution can be considered to be a first colormetric solution.

A plurality of ampules 48, 50 and 52 are contained within recesses 18, 20 and 22, respectively. Ampule 50 includes a white indicator band W and contains 0.5 ml of a 20% solution of morpholine ($NH(CH_2)_2OCH_2CH_2$) in distilled water. Ampule 48 is identified by a red band R and contains 0.5 ml of a 5% solution of sodium nitroprusside also termed sodium nitroferricyanide ($Na_2Fe(CN)_5(NO).2H_2O$) in distilled water. Ampule 52 is identified by a blue band B and contains 1 ml of an acidified permanganate solution comprising equal volumes of 1.0N potassium permanganate ($KMnO_4$) and sulphuric acid ($H_2SO_4$) in distilled water.

The petroleum alcohol test kit 10 further includes an indicator cap 56 which is positioned within circular recess 28. Indicator cap 56 includes a base 58 and integral circular sidewalls 60. Base 58 further includes an aperture 62 and a circular piece of paper 64 is affixed to the inner circular surface of base 58 so as to cover the aperture 62. A mixing cup 68 is contained within circular recess 32. A graduated cylinder 70 having a cork 72 selectively positioned within the open end thereof is contained within elongated recess 26. A pipette 74 is contrived within cylinder 70.

In conducting an on site test of a petroleum product, the graduated cylinder 70 should be filled with 100 ml of the petroleum product which in the specific embodiment would constitute the cylinder 70 being filled to the "Fill Line". The contents of tubular container 44, which is the ethylene glycol-methyl violet dye solution, should then be added to the graduated cylinder, the cork positioned within the opening to seal the cylinder, and the cylinder should then be shaken for approximately fifteen seconds. The cylinder should then be placed into circular recess 34 so that the cylinder is generally vertically disposed in a stable condition. The contents of the graduated cylinder should be allowed to settle for at least one minute. The level of the purple alcohol layer at the bottom of the cylinder should then be read wherein one scale division on the cylinder equals 1% alcohol content in the petroleum product. The test that is conducted is along the lines of the test set out at Section X8 of the 1981 Annual Book of ASTM Standards, Part 23, "Petroleum Products and Lubricants(1)", pp. 935-936, ASTM Philadelphia (1981).

To determine the type of alcohol, either ethanol ($C_2H_5OH$) or methanol ($CH_3OH$), present in a petroleum product sample, the following steps should be performed. The contents of ampule 50 (20% solution of morpholine in distilled water) and the contents of ampule 48 (5% solution of sodium nitroprosside in distilled water) should be mixed together in mixing cup 68 to form a second colorimetric solution which is utilized to impregnate paper 64 contained in indicator cap 56.

A sample of the petroleum product should be introduced into container 40 up to the fill line which equates to 1 ml. Pipette 74 can be used to obtain the sample and introduce it into the container 40. The contents of ampule 52 (acidified permanganate solution) should be added to the petroleum product sample in container 40 and cap 42 securely attached to container 40. Container 40 should then be shaken for approximately ten seconds. Cap 42 should be removed and replaced with indicator cap 56 having the impregnated paper 64 contained therein.

The acidified permanganate will react with ethyl alcohol to form acetaldehyde in vapor form. Acetaldehyde vapor reacts with an equal mixture of sodium nitroprosside and morpholine to produce a blue stain. Thus, if ethanol is present, a blue stain will appear on the paper 64 in the cap 56 at once or within a few minutes. The depth of the color and the time it takes for the color develop will depend upon the quantity of ethanol present. The acidified potassium permanganate will react with methyl alcohol to form formaldehyde in vapor form. Formaldehyde vapor does not produce any color when it reacts with the second colorimetric solution. Thus, if no color develops within five to ten minutes, methanol is the alcohol present as an additive in the petroleum sample.

If the petroleum product contains a mixture of ethyl alcohol and methyl alcohol, then the color will be somewhere between a dark blue and no color. The depth of color is dependent upon the volume of ethyl alcohol present. The examples set out below will provide guidelines to equating color with alcohol content.

EXAMPLES DIRECTED TO DETECTION OF THE AMOUNT OF ALCOHOL PRESENT IN A PETROLEUM PRODUCT

Twelve samples of petroleum products, each comprised of gasoline and alcohol, were tested to determine the amount of alcohol (ethanol and methanol) present in the petroleum product. The testing was done in accordance with the invention wherein 10 ml of the ethylene glycol-methyl violet dye solution was added to 100 ml of the petroleum product contained in the graduated cylinder (70). The alcohol content was read by the graduations. The table set out below sets forth the results of the testing.

TABLE I

Test Results for Alcohol Detection Tests

| Sample | Source | Results |
|---|---|---|
| 1 | Commercial ethanol blend from Station A | 9.5 (v/o alcohol recovered within 1 minute)* |
| 2 | Commercial ethanol blend from Station A | 9.5 (v/o alcohol recovered within 1 minute)** |
| 3 | Commercial ethanol blend from Station B | 10 (v/o alcohol recovered within 1 minute)* |
| 4 | Commercial ethanol blend from Station B | 9.5 (v/o alcohol recovered within 1 minute)** |
| 5 | Laboratory blend of 10 v/o ethanol and 90 v/o gasoline | 9.5 v/o* |
| 6 | Laboratory blend of 10 v/o ethanol and 90 v/o gasoline | 10 v/o** |
| 7 | Laboratory blend of 10 v/o methanol and 90 v/o gasoline | 10 v/o* |
| 8 | Laboratory blend of 10 v/o methanol and 90 v/o gasoline | 10 v/o** |
| 9 | Laboratory blend of 5 v/o ethanol and 95 v/o gasoline | 4.5 v/o* |
| 10 | Laboratory blend of 5 v/o ethanol and 95 v/o gasoline | 5.0 v/o** |
| 11 | Laboratory blend of 5 v/o methanol and 5 v/o ethanol and 90 v/o gasoline | 10 v/o* |
| 12 | Laboratory blend of 5 v/o methanol and 5 v/o ethanol and 90 v/o gasoline | 10 v/o** |

*Tested with a solution of ethylene glycol and methyl violet dye over one year old.
**Tested with a freshly prepared solution of ethylene glycol and methyl violet dye.

EXAMPLES DIRECTED TO DETECTION OF THE TYPE OF ALCOHOL (ETHANOL OR METHANOL) PRESENT IN A PETROLEUM PRODUCT

Six samples of petroleum products, each comprised of gasoline and alcohol, were tested to determine the type of alcohol present in the petroleum product. The testing was conducted in accordance with the invention wherein 0.5 ml of a 20% solution of morpholine in distilled water and 0.5 ml of a 5% solution of sodium nitroprusside in distilled water were mixed together in a cup (68) to form a wetting solution more than one year old from the date of the tests. This wetting solution was used to wet the paper 64 contained in cap 56. The table set out below sets forth the results of the testing:

TABLE II

Test Results for Alcohol Detection Tests

| Sample | Source | Results |
|---|---|---|
| 1 | Commercial ethanol blend from Station A | Within 5 minutes a medium to dark blue developed |
| 2 | Commercial ethanol blend from Station B | Very dark blue developed within 4½ minutes |
| 3 | Laboratory blend of 10 v/o ethanol and 90 v/o gasoline | Very dark blue developed within 4 minutes |
| 4 | Laboratory blend of 10 v/o methanol and 90 v/o gasoline | No color developed |
| 5 | Laboratory blend of 10 v/o methanol and 90 v/o gasoline | No color developed |
| 6 | Laboratory blend of 5 v/o methanol, 5 v/o ethanol and 90 v/o gasoline | Within 5 minutes a medium blue color developed |

TABLE III

| Sample | Source | Test for Presence of Alcohol* | Test for Volume of Ethanol** |
|---|---|---|---|
| 1 | Gasohol sample from service station X | 8 v/o alcohol within 30 sec. 9 v/o alcohol within 2 min. 9.5 v/o alcohol within 10 min. | Faint blue developed in 1 minute; noticed separation of phases probably caused by not vigorous enough sample and reagent mixing. |

TABLE III-continued

| Sample | Source | Test for Presence of Alcohol* | Test for Volume of Ethanol** |
|---|---|---|---|
| | | | After shaking vigorously, deep blue color appeared within 3 minutes. |
| 2 | Gasoline (regular) sample from service station X | less than 1 v/o alcohol within 30 sec. less than 1 v/o alcohol within 2 min. | No color change |
| 3 | Gasohol sample from service station Y | 10 v/o alcohol within 30 sec. 10.5 v/o alcohol within 2 min. | Faint blue color within 45 seconds and deep blue color within 3-5 minutes. |
| 4 | Gasoline (regular) sample from service station Y | less than 1 v/o alcohol within 30 sec. less than 1 v/o alcohol within 2 min. | No color change |
| 5 | Gasoline (no lead) sample from service station Y | 1 v/o alcohol within 30 sec. | No color change |

*5 ml of ethyl glycol-methyl violet dye solution (100 ml ethyl glycol + 10 drops methyl violet dye) were placed in 50 ml of petroleum product and the content read on a graduated cylinder proportional for 55 ml of test solution.

FIGS. 4 through 7 illustrate a second embodiment of the kit of the invention. Most of the components contained in the second embodiment are common to the first embodiment, and will be identified by the same reference numeral.

Referring to FIG. 4, the kit is generally designated as 80. Kit 80 includes a styrofoam container 82 having a base 84 with a plurality of recesses, which will be discussed later, and an integral fold-over flap 86. The interior surface 88 of the flap 86 has a set of instructions 90 affixed thereto. The interior surface 92 of the base 84 has a plurality of recesses which will be discussed hereinafter.

An elongate recess 94 is contained in the base near the top edge thereof, and has enlarged portions 96 and 98 at the opposite ends thereof. A pair of pipettes 100, 102 are positioned within the elongate recess 94 so that their bulb portions rest within the enlarged portions. Another recess 106 is contained within the base adjacent the enlarged portion 98. Indicator cap 56 is contained within recess 106. One pipette 100 is used to obtain a 1 ml sample of the petroleum product when testing for the kind of alcohol present. The other pipette 102 is used to impregnate paper 64 contained in indicator cap 56.

A plurality of generally vertically aligned recesses 108, 110, 112 are contained in base 84 adjacent the left edge thereof. Ampules 48, 50 and 52 are contained in recesses 108, 110 and 112, respectively. An elongate recess 114 is contained in base 84 and is positioned below recess 106. A mixing cup 116 is positioned within elongate recess 114. Mixing cup 116 performs the same function as mixing cup 68 in the first embodiment. Another elongate recess 120 is contained in the interior surface of the base and is positioned vertically below the recess 114. Elongate recess 120 has a pair of horizontally spaced circular recesses 122, 124 contained therein adjacent one end thereof. Although not illustrated, tubular container 40 is to be positioned within recess 120. Circular recesses 122 and 124 are to be used as recesses into which the lower end of container 40 can be inserted to maintain container 40 in an upright, generally vertical disposition during use.

Cylinder 70 is contained within elongate rectangular box 126. Tubular container 44 is contained within cylinder 70. Fold-over flap 86 can be folded over base 84 so that container 82 can be slipped into sleeve 128. The sleeve, containing the container 82, and the rectangular box 126 are positioned within a box. The lower half of the box 130 with the sleeve 128 and box 126 positioned therein is illustrated in FIG. 7.

While there have been described above the principles of this invention in connection with specific apparatus, it is to be clearly understood that this description is made only by way of example and not as a limitation to the scope of the invention.

What is claimed is:

1. A test kit for on site testing of petroleum for alcohol content comprising:
   a calibrated reaction cylinder;
   a first tube of ethylene glycol and methyl violet color indicator, a second tube having an opening sealably closable by a lid means, and a first lid means for removably sealing said opening;
   a first vial of 20% solution of morpholine in distilled water;
   a second vial of 5% solution of sodium nitroprusside in distilled water;
   a mixing cup for mixing the contents of said first and second vials to make an indicating fluid;
   a second lid means for removably sealing said opening in said second tube, said second lid means including a fluid-absorbent paper or fabric adapted to be impregnated with the indicating fluid;
   a third vial of potassium permanganate and sulfuric acid in distilled water; and
   a carrier is adapted to receive and carry said first tube, said second tube with the first lid means attached, said first, second and third vials, said mixing cup, said second lid means, and said calibrated reaction cylinder.

2. The test kit of claim 1 wherein said calibrated reaction cylinder includes a fill indicator to indicate the level to which the petroleum should be filled in said cylinder.

3. The test kit of claim 2 wherein said cylinder further includes a plurality of calibrations to indicate various amounts of alcohol content of the petroleum.

4. The test kit of claim 1 wherein said carrier contains a recess adapted to securely receive the closed end of said reaction cylinder so as to hold it in a generally vertical position.

5. The test kit of claim 1 wherein said carrier contains a recess adapted to securely receive the closed end of said second tube so as to hold it in a generally vertical position.

6. The test kit of claim 1 further including a set of instructions affixed thereto.

7. The test kit of claim 1 wherein said first, second and third vials are each disposable vials.

8. The test kit of claim 1 wherein said second lid means includes a cap having a circular top member and an integral depending cylindrical member, said cylindrical member being internally threaded so as to be threadably receivable onto said second tube, and said top member containing an aperture therein in which said fluid-absorbent paper or fabric is positioned.

9. A test kit for on site testing of gasohol for the presence of ethyl alcohol comprising:
a reaction tube having an opening sealably closable by a lid means, and a first lid means for removably sealing said opening;
a first vial of 20% solution of morpholine in distilled water, and a second vial of 5% solution of sodium nitroprusside in distilled water;
a mixing cup for mixing the contents of said first and second vials to make an indicating fluid;
a second lid means for removably sealing said opening in said reaction tube, said second lid means including a fluid-absorbent paper or fabric adapted to be impregnated with the indicating fluid;
a third vial of potassium permanganate and sulfuric acid in distilled water; and
a carrier is adapted to receive and carry said reaction tube with the first lid means attached, said first, second and third vials, said a mixing cup and said second lid means.

10. The test kit of claim 9 wherein said carrier contains a recess adapted to securely receive the closed end of said reaction tube so as to hold it in a generally vertical position.

11. The test kit of claim 9 further including a set of instructions affixed thereto.

12. The test kit of claim 9 wherein said first, second and third vials are each snap-off top glass ampules.

13. The test kit of claim 9 wherein said second lid means includes a cap having a circular top member and an integral depending cylindrical member, said cylindrical member being internally threaded so as to be threadedly receivable onto said reaction tube, and said top member containing an aperture therein in which said fluid-absorbent paper of fabric is positioned.

14. A method for on site testing of petroleum for alcohol content comprising the steps of:
mixing a first sample of the petroleum with a first colorimetric reagent solution of ethylene glycol and methyl violet dye in a graduated cylinder;
positioning said graduated cylinder in a generally vertical position;
observing the mixed contents of said cylinder for the presence of a colored portion wherein the colored portion is indicative of the presence of ethyl alcohol or methyl alcohol alone or together in the petroleum;
measuring the height of said colored portion to determine the amount of alcohol in the petroleum sample;
mixing a 20% solution of morpholine in distilled water with a 5% solution of sodium nitroprusside in distilled water to form a second reagent colorimetrically and selectively responsive to the pressure of ethyl alcohol and non-responsive to the presence of formaldehyde;
impregnating a fabric with said second colorimetric reagent;
mixing a solution of potassium permanganate and sulfuric acid in distilled water with a second sample of petroleum;
contacting said fabric with vapors emitted by the mixture of said potassium permanganate-sulfuric acid solution and second sample of petroleum; and
observing the color of the colorimetric reagent, a color change in response to the presence of ethyl alcohol and an absence of color change in response to the absence of ethyl alcohol in said second sample of petroleum.

15. The method of claim 14 wherein the volumetric ratio of said first gasoline sample to said colorimetric reagent solution is 10:1.

16. The method of claim 14 wherein said colorimetric reagent solution is comprised of 2% by volume of the methyl violet dye and 98% by volume of the ethylene glycol.

17. A method for on site testing of gasohol for the presence of ethyl alcohol comprising the steps of:
mixing a 20% solution of morpholine in distilled water with a 5% solution of sodium nitroprusside in distilled water to form a reagent colorimetrically and selectively responsive to the presence of ethyl alcohol and non-responsive to the presence of formaldehyde;
impregnating a fabric with said colorimetric reagent;
mixing a solution of potassium permanganate and sulfuric acid in distilled water with a gasohol sample;
contacting said fabric with vapors emitted by the mixture of said potassium permanganate-sulfuric acid solution and gasohol; and
observing the color of the colorimetric reagent, a color change in response to the presence of ethyl alcohol and an absence of color change in response to the presence of methyl alcohol.

18. A test kit for on site testing of petroleum for alcohol content comprising:
a calibrated reaction cylinder removably contained within an elongate box;
a first tube of ethylene glycol and methyl violet color indicator, a second tube having an opening sealably closable by a lid means, and a first lid means for removably sealing said opening, said first tube being contained within said calibrated reaction cylinder;
a first vial of 20% solution of morpholine in distilled water;
a second vial of 5% solution of sodium nitroprusside in distilled water;
a mixing cup for mixing the contents of said first and second vials to make an indicating fluid;
a second lid means for removably sealing said opening in said second tube, said second lid means including a fluid-absorbent paper or fabric adapted to be impregnated with the indicating fluid;
a third vial of potassium permanganate and sulfuric acid in distilled water;
a carrier is adapted to receive and carry said second tube with the first lid means attached, said first, second and third vials, said mixing cup, said second lid means;
said carrier being slideable into a sleeve to form a sleeve-carrier assembly; and
said elongate box and sleeve-carrier assembly positioned within a container.

* * * * *